(12) United States Patent
Click et al.

(10) Patent No.: US 9,095,394 B2
(45) Date of Patent: Aug. 4, 2015

(54) CEMENT DELIVERING DEVICE AND METHOD

(75) Inventors: Bryan Click, Fremont, CA (US); Brian Donovan, San Jose, CA (US)

(73) Assignee: KYPHON SARL, Neuchatel (CH)

( * ) Notice: Subject to any disclaimer, the term of this patent is extended or adjusted under 35 U.S.C. 154(b) by 515 days.

(21) Appl. No.: 13/456,597

(22) Filed: Apr. 26, 2012

(65) Prior Publication Data

US 2013/0289571 A1    Oct. 31, 2013

(51) Int. Cl.
*A61B 17/58* (2006.01)
*A61B 17/88* (2006.01)
*A61M 5/315* (2006.01)
*A61M 5/20* (2006.01)

(52) U.S. Cl.
CPC ......... *A61B 17/8827* (2013.01); *A61B 17/8802* (2013.01); *A61B 17/8805* (2013.01); *A61B 17/8822* (2013.01); *A61M 5/2053* (2013.01); *A61M 5/315* (2013.01)

(58) Field of Classification Search
CPC ........... A61B 17/8802; A61B 17/8805; A61B 17/8811; A61B 17/8819; A61B 17/8822; A61M 5/2033; A61M 5/2053; A61M 5/2066; A61M 5/315; A61M 5/31501; A61M 5/31513; A61M 5/31515; A61M 5/3153; A61M 5/31536; A61M 5/31561; A61M 5/31563
USPC ................. 606/92–94; 604/89, 91, 236–238; 222/252, 336, 339, 340, 386, 387, 510
See application file for complete search history.

(56) References Cited

U.S. PATENT DOCUMENTS

| | | | |
|---|---|---|---|
| 2,841,145 A * | 7/1958 | Epps ............................... | 604/89 |
| 4,563,174 A * | 1/1986 | Dupont et al. .................. | 604/89 |
| 5,527,284 A * | 6/1996 | Ohnemus et al. ............. | 604/110 |
| 5,785,683 A * | 7/1998 | Szapiro et al. .................. | 604/89 |
| 6,439,439 B1 | 8/2002 | Rickard et al. | |
| 6,599,293 B2 | 7/2003 | Tague et al. | |
| 7,008,433 B2 | 3/2006 | Voellmicke et al. | |
| 7,112,205 B2 | 9/2006 | Carrison | |
| 7,811,291 B2 | 10/2010 | Liu et al. | |
| 2005/0105384 A1 | 5/2005 | Eder et al. | |
| 2009/0131948 A1 | 5/2009 | Liu et al. | |
| 2009/0171361 A1* | 7/2009 | Melsheimer et al. ........... | 606/93 |
| 2012/0041366 A1* | 2/2012 | Fayyaz et al. .................. | 604/89 |

* cited by examiner

Primary Examiner — Michael T Schaper
Assistant Examiner — Tracy Kamikawa
(74) Attorney, Agent, or Firm — Sorell Lenna & Schmidt LLP (57) ABSTRACT

A delivery system includes a reservoir for storing pressurized fluid and a piston rod passing through the reservoir and having an end portion with a dimension larger than the piston rod. A sleeve is configured to engage the end portion of the piston rod such that when the piston rod is advanced, the end portion seals an opening in the sleeve. The sleeve and the end portion function as a piston for extracting fluid from a delivery chamber. When the piston rod is retracted, the sleeve engages a portion of the end portion to permit the reservoir to communicate with the delivery chamber through the opening. Methods of use are disclosed.

21 Claims, 3 Drawing Sheets

CEMENT DELIVERING DEVICE AND METHOD

TECHNICAL FIELD

The present disclosure generally relates to medical devices for the treatment of musculoskeletal disorders, and more particularly to a surgical system and method for delivering cement or other materials.

BACKGROUND

Many medical procedures employ medical grade cement in connection with the restoration and strengthening of bone structures. During such procedures, cement is typically dispensed to a bone to fill in voids or spaces in the bone or between medical devices or implants attached to or embedded within the bone. These dispensing devices may include systems as simple as syringes and as complex as electronically controlled values.

Due to the medical nature of some procedures, the amount and placement of the fluids, such as, cement, needs to be supervised carefully. Despite the simplicity or complexity of the dispensing system, control over when, where and how much cement is dispensed is of concern. This disclosure describes improvements over these prior art technologies in providing better control for dispensing fluids, in particular, with respect to applications where greater valve control is needed.

SUMMARY

Accordingly, a surgical system and method for delivering fluid, such as cement to a bone are provided. In one embodiment, in accordance with the principles of the present disclosure, a delivery system is provided. The system comprises a reservoir for storing pressurized fluid and a piston rod passing through the reservoir and having an end portion with a dimension larger than the piston rod.

A sleeve is configured to engage the end portion of the piston rod such that when the piston rod is advanced, the end portion seals an opening in the sleeve. The sleeve and the end portion function as a piston for ejecting fluid from a delivery chamber. When the piston rod is retracted, the sleeve engages a portion of the end portion to permit the reservoir to communicate with the delivery chamber through the opening.

In one embodiment, the system comprises a delivery system, including a reservoir for storing pressurized fluid and a biased reservoir piston configured to pressurize fluid in the reservoir. The reservoir piston is biased by a spring disposed within a body in fluid communication with the reservoir. A piston rod passes through the reservoir and has a ball-shaped end portion with a dimension larger than the piston rod. A sleeve is configured to engage the end portion of the piston rod. The sleeve includes an outer portion that contacts an internal bore of a delivery chamber, at least two opposing supports that are configured to engage the end portion of the piston rod and an engagement portion on each support being configured to occupy a fraction of a surface area of the end portion of the piston rod. When the piston rod is advanced, the end portion seals an opening in the sleeve, and the sleeve and the end portion function as a piston for ejecting fluid from the delivery chamber. When the piston rod is retracted, the sleeve engages a portion of the end portion to permit the reservoir to communicate with the delivery chamber through the opening and force fluid into the delivery chamber.

In one embodiment, a method for delivering bone cement includes the steps of: providing a delivery system including a reservoir for storing pressurized fluid, a piston rod passing through the reservoir and having an end portion with a dimension larger than the piston rod, and a sleeve configured to engage the end portion of the piston rod such that when the piston rod is advanced, the end portion seals an opening in the sleeve, and the sleeve and the end portion function as a piston for ejecting fluid from a delivery chamber, and when the piston rod is retracted, the sleeve engages a portion of the end portion to permit the reservoir to communicate with the delivery chamber through the opening, and reciprocating the piston rod to alternately fill and dispense fluid from the delivery chamber.

BRIEF DESCRIPTION OF THE DRAWINGS

The present disclosure will become more readily apparent from the specific description accompanied by the following drawings, in which.

Like reference numerals indicate similar parts throughout the figures.

DETAILED DESCRIPTION

The exemplary embodiments of a surgical system and related methods of use disclosed are discussed in terms of medical devices for the treatment of musculoskeletal disorders and more particularly, in terms of a surgical system and method for delivering cement or other materials during a procedure. It is envisioned that the surgical system and method may be employed in applications such as repairing cracks, fissures, fractures, etc. rebuilding bone or securing prosthetic joints, pins, or other devices in bones.

In one embodiment, the surgical system provides a cement delivery device that delivers cement or other material from a single reservoir while limiting a high-pressure region to a small diameter delivery chamber. A reciprocating piston may be mechanically actuated from outside of a fluoroscopy field. During a delivery stroke, a piston with a ball end seals against a sleeve and is driven to deliver cement. As the piston and sleeve are retracted, a valve opens and cement is forced from a main reservoir into the delivery chamber. Driving a smaller diameter section of cement reduces a force necessary to generate delivery pressures, allowing for a wider range of actuation mechanisms. Limiting the high-pressure regions of the device contributes to overall safety and manufacturability. A positive displacement fill minimizes lag-time between actuations and permits for partial strokes.

It is contemplated that one or all of the components of the surgical system may be disposable, peel-pack, pre-packed sterile devices. One or all of the components of the surgical system may be reusable. The surgical system may be configured as a kit with multiple sized and configured components.

It is envisioned that the present disclosure may be employed to treat or repair bones damaged through injuries, disorders, abnormalities and/or surgery. In one particularly useful embodiment, spinal disorders or repairs such as, for example, osteoporosis, curvature abnormalities, tumors, fractures, etc. may be repaired. It is contemplated that the present disclosure may be employed with other osteal and bone related applications, including those associated with diagnostics and therapeutics. It is further contemplated that the disclosed surgical system and methods may be alternatively employed in a surgical treatment with a patient in a prone or supine position, and/or employ various surgical approaches to the spine, including anterior, posterior, posterior mid-line, direct lateral, postero-lateral, and/or antero-lateral approaches, and in other body regions. The present disclosure may also be alternatively employed with procedures for treating the lumbar, cervical, thoracic and pelvic regions of a spinal column. The system and methods of the present disclosure may also be used on animals, bone models and other non-living substrates, such as, for example, in training, testing and demonstration.

The present disclosure may be understood more readily by reference to the following detailed description of the disclosure taken in connection with the accompanying drawing figures, which form a part of this disclosure. It is to be understood that this disclosure is not limited to the specific devices, methods, conditions or parameters described and/or shown herein, and that the terminology used herein is for the purpose of describing particular embodiments by way of example only and is not intended to be limiting of the claimed disclosure. Also, as used in the specification and including the appended claims, the singular forms "a," "an," and "the" include the plural, and reference to a particular numerical value includes at least that particular value, unless the context clearly dictates otherwise. Ranges may be expressed herein as from "about" or "approximately" one particular value and/or to "about" or "approximately" another particular value. When such a range is expressed, another embodiment includes from the one particular value and/or to the other particular value. Similarly, when values are expressed as approximations, by use of the antecedent "about," it will be understood that the particular value forms another embodiment. It is also understood that all spatial references, such as, for example, horizontal, vertical, top, upper, lower, bottom, left and right, are for illustrative purposes only and can be varied within the scope of the disclosure. For example, the references "upper" and "lower" are relative and used only in the context to the other, and are not necessarily "superior" and "inferior".

Further, as used in the specification and including the appended claims, "treating" or "treatment" of a disease or condition refers to performing a procedure that may include administering one or more drugs to a patient (human, normal or otherwise or other mammal), in an effort to alleviate signs or symptoms of the disease or condition. Alleviation can occur prior to signs or symptoms of the disease or condition appearing, as well as after their appearance. Thus, treating or treatment includes preventing or prevention of disease or undesirable condition (e.g., preventing the disease from occurring in a patient, who may be predisposed to the disease but has not yet been diagnosed as having it). In addition, treating or treatment does not require complete alleviation of signs or symptoms, does not require a cure, and specifically includes procedures that have only a marginal effect on the patient. Treatment can include inhibiting the disease, e.g., arresting its development, or relieving the disease, e.g., causing regression of the disease. For example, treatment can include reducing acute or chronic inflammation; alleviating pain and mitigating and inducing re-growth of new ligament, bone and other tissues; as an adjunct in surgery; and/or any repair procedure. Also, as used in the specification and including the appended claims, the term "tissue" includes soft tissue, ligaments, tendons, cartilage and/or bone unless specifically referred to otherwise.

The following discussion includes a description of a surgical system and related methods of employing the surgical system in accordance with the principles of the present disclosure. Alternate embodiments are also disclosed. Reference will now be made in detail to the exemplary embodiments of the present disclosure, which are illustrated in the accompanying figures. Turning now to FIGS. 1-4, there is illustrated components of a surgical system, such as, for example, a cement delivery system 10 in accordance with the principles of the present disclosure.

The components of delivery system 10 can be fabricated from biologically acceptable materials suitable for medical applications, including metals, synthetic polymers, ceramics and bone material and/or their composites, depending on the particular application and/or preference of a medical practitioner. For example, the components of delivery system 10, individually or collectively, can be fabricated from materials such as stainless steel alloys, commercially pure titanium, titanium alloys, Grade 5 titanium, superelastic titanium alloys, cobalt-chrome alloys, stainless steel alloys, superelastic metallic alloys (e.g., Nitinol, super elasto-plastic metals, such as GUM METAL® manufactured by Toyota Material Incorporated of Japan), ceramics and composites thereof such as calcium phosphate (e.g., SKELITE™ manufactured by Biologix Inc.), thermoplastics such as polyaryletherketone (PAEK) including polyetheretherketone (PEEK), polyetherketoneketone (PEKK) and polyetherketone (PEK), carbon-PEEK composites, PEEK-BaSO$_4$ polymeric rubbers, polyethylene terephthalate (PET), fabric, silicone, polyurethane, silicone-polyurethane copolymers, polymeric rubbers, polyolefin rubbers, hydrogels, semi-rigid and rigid materials, elastomers, rubbers, thermoplastic elastomers, thermoset elastomers, elastomeric composites, rigid polymers including polyphenylene, polyamide, polyimide, polyetherimide, polyethylene, epoxy, bone material including autograft, allograft, xenograft or transgenic cortical and/or corticocancellous bone, and tissue growth or differentiation factors, partially resorbable materials, such as, for example, composites of metals and calcium-based ceramics, composites of PEEK and calcium based ceramics, composites of PEEK with resorbable polymers, totally resorbable materials, such as, for example, calcium based ceramics such as calcium phosphate, tri-calcium phosphate (TCP), hydroxyapatite (HA)-TCP, calcium sulfate, or other resorbable polymers such as polyaetide, polyglycolide, polytyrosine carbonate, polycaroplaetohe and their combinations. Various components of delivery system 10 may have material composites, including the above materials, to achieve various desired characteristics such as strength, rigidity, elasticity, compliance, biomechanical performance, durability and radiolucency or imaging preference. The components of delivery system 10, individually or collectively, may also be fabricated from a heterogeneous material such as a combination of two or more of the above-described materials. The components of delivery system 10 may be monolithically formed, integrally connected or include fastening elements and/or instruments, as described herein.

Figure 1:
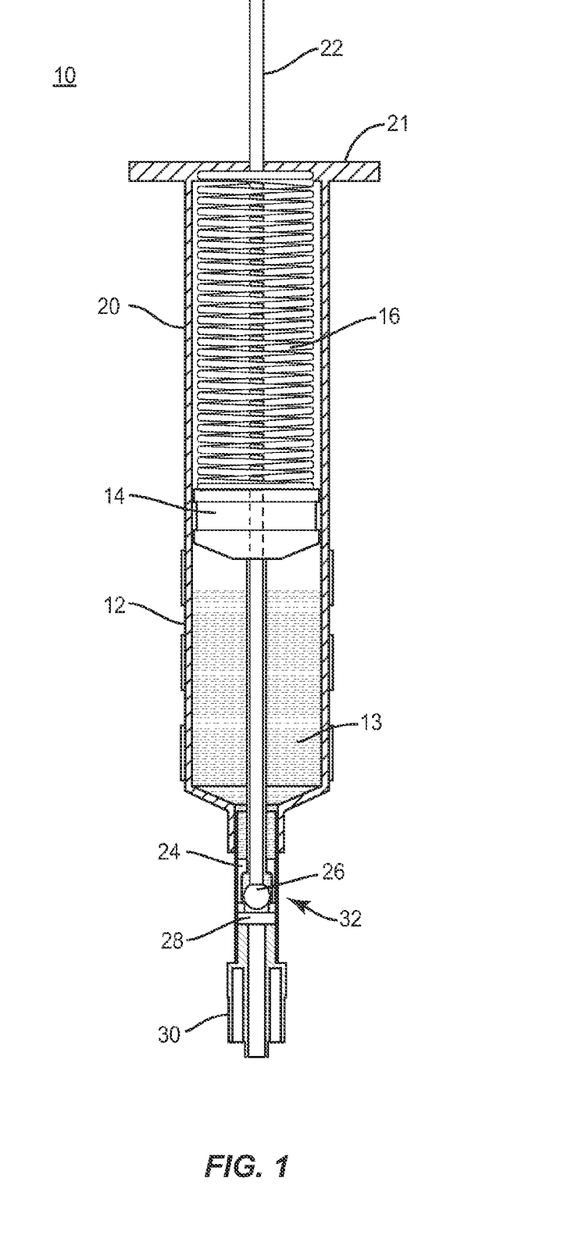
FIG. 1 is a side view of one embodiment of a delivery system with some parts in phantom to show internal components in accordance with the principles of the present disclosure.

Delivery system 10 is employed, for example, with an open, mini-open or minimally invasive surgical technique to apply bone cement or other fluidized material to a bone, such as, for example, a vertebra of a spine. Delivery system 10 includes a housing or body 20, which provides support and contains components of the delivery system 10. A spring 16 is provided in an upper portion of the body 20 and is fixed to an end portion 21. Other biasing mechanisms are also contemplated and may include spring-like materials or structures. The spring 16 biases a reservoir piston 14 to provide pressure on a fluidized material 13 (e.g., cement) disposed in a main reservoir 12.

A piston rod 22 passes through the body 20 and the end portion 21. Portions of components of the delivery system 10 are depicted in phantom so that internal components may be seen. For example, the piston rod 22 is shown passing through the entire dispensing system 10. Piston rod 22 includes a ball-shaped end portion or ball end 26, which is disposed within a sleeve 24. The ball end 26 is shown as having a spherical shape. It is contemplated that other shapes may also be employed for the ball end 26. The sleeve 24 includes an upper opening that has a clearance fit with the piston rod 22 and an interference fit with the ball end 26. A lower opening of the sleeve 24 has an interference fit with ball-shaped end portion 26. This relationship between the sleeve 24 and the piston ball 26 permits the piston ball 26 to function as a valve and a piston for delivering cement as will be explained in greater detail herein.

When the piston rod 22 is driven in the downward direction to deliver cement 13, the ball end 26 seals against the sleeve 24 (at the lower portion), and cement 13 is driven from a delivery chamber 28 through a fitting 30 or other dispensing structure (e.g., a back flow device (not shown)). The fitting 30 may include a Luer fitting, for example. The Luer fitting is a standardized system of small-scale fluid fittings used for making leak-free connections between a male-taper fitting and its mating female part on medical and laboratory instruments, including hypodermic syringe tips and needles or stopcocks and needles. The Luer fitting 30 may receive a needle, syringe, nozzle, etc. (not shown) to dispense the cement 13. During a stroke of the piston rod 22, cement 13 from the main reservoir 12, which is pressurized by the spring 16 that is attached to the main reservoir piston 14, flows in to fill a volume displaced by a piston assembly 32 formed by the ball end 26 sealing against the sleeve 24. During retraction of the piston assembly 32, cement 13 is displaced from the main reservoir 12 into the delivery chamber 28. This is due to the pressurized cement 13 in the main reservoir 12 passing around the ball end 26 and through the interior of the sleeve 24.

Bone cement is typically mixed prior to delivery to the surgical site and delivered in a fluid state. That is, powdered bone cement material is often mixed with a fluid such as water to produce a pasty cement material that hardens upon curing. The viscosity of the bone cement is dependent on the amount of water present in the cement mixture and increases as time elapses after mixing due to curing of the cement. Eventually, the cement hardens to a solid material. The less water in the cement, the more viscous the material and the higher the build up of pressures in the delivery device. Controlling the pressure build up in the delivery device is essential in preventing rupturing of the delivery device, limiting potential injury to the surgeon and for preventing leakage of the cement into the surgical site. Controlling the pressure build up in the delivery device is also important for the precise and proper delivery of the cement to the desired area.

Accordingly, delivery system 10 permits high viscosity cement 13, e.g., poly(methyl methacrylate) (PMMA) or other types of cement, to be delivered into a bone, e.g., a vertebral body, by actuation of the piston rod 22. The piston rod 22 may be activated manually or automatically. In one embodiment, the piston rod 22 is activated from outside a fluoroscopy field if fluoroscopy is employed for imaging during a procedure. The activation of the piston rod 22 is preferably performed without using multiple devices or accessories.

By employing the spring 16 to bias the reservoir piston 14, high-pressure regions are eliminated resulting in increased safety to the physician. In other systems, hydraulic and pneumatic systems may develop high pressures in the reservoir, which could potentially cause cement to explode out of the dispensing device under certain conditions. The present embodiments act as an alternative to using hydraulics to drive a floating or reciprocating piston. This increases physician safety and simplifies the product.

In accordance with the present principles, the delivery system 10 is able to deliver cement by mechanically driving the reciprocating piston assembly 32 via remote actuation (e.g., a push-pull cable, etc.). The piston assembly 32 acts as a piston, a valve and a positive displacement fill mechanism. The piston assembly 32 will be shown and described in greater detail in FIGS. 2-4.

Figure 2:
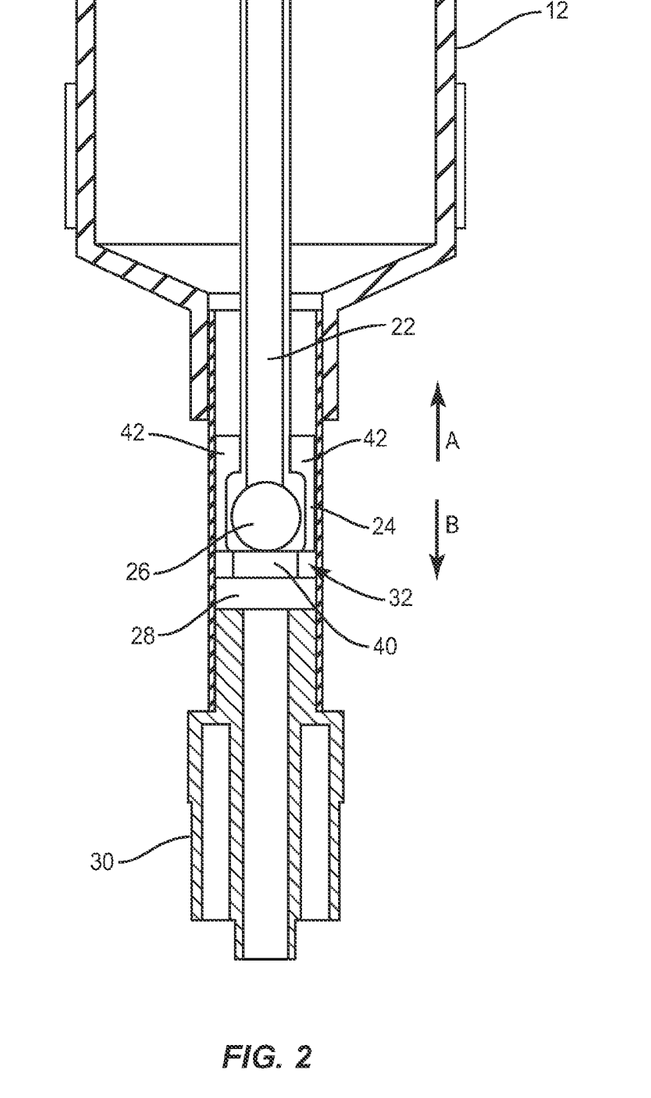
FIG. 2 is a magnified view of the components of the system shown in FIG. 1 showing details of a piston assembly formed with an end portion of a piston rod and a sleeve in accordance with the present principles.

Referring to FIG. 2, a magnified view of a distal end portion of the delivery system 10 of FIG. 1 is shown. The piston rod 22 with the ball end 26 and the sleeve 24 function in two modes. A first mode is for filling the delivery chamber 28. The piston rod 22 is retracted in the direction of arrow "A". As the ball end 26 is retracted, an opening 40 in the sleeve 24 is no longer sealed off from the delivery chamber 28. Pressurized cement 13, being biased by the spring 16, is sent from the reservoir 12 passed the ball end 26 and the sleeve 28 through the opening 40 to the delivery chamber 28. The delivery chamber 28 fills with the cement 13 to await dispensing during a procedure.

In a second mode, cement 13 is dispensed from the delivery chamber 28 when the piston rod 22 is moved in the direction of arrow "B". The ball end 26 of the piston rod 22 engages the opening 40. The ball end 26 engages surfaces of the opening 40 to form a seal to prevent cement from moving into or out of the opening 40. As movement in the direction of arrow "B" continues, the ball end 26 of the piston rod 22 remains engaged with the opening 40 and begins to impart motion to the sleeve 24 as well. The ball end 26 and the sleeve 24 work together to form a piston to eject cement 13 from the delivery chamber 28. The piston assembly 32 moves in unison to force the cement 13 from the delivery chamber 28 to dispense the cement 13 through the fitting 30. When cement 13 is dispensed, the pressure on the delivery side closes a valve formed by the ball end 26 in the opening 40 of the sleeve 24, restricting the high-pressure region of the system 10 to the delivery chamber 28. When the piston is again retracted in the direction of arrow "A", the ball end 26 and sleeve 24 decouple for a short time, opening the valve to the main reservoir 12. As the piston rod 22 continues to retract, cement is again displaced from the main reservoir 12 into the delivery chamber 28. This positive displacement minimizes lag-time between actuations and allows for partial strokes.

The delivery system 10 permits partial strokes and therefore less than a full volume of the dispensing chamber 28 may be dispensed. For example, when the piston rod 22 is advanced less than a full stroke, the delivery chamber 28 delivers fluid occupying less than its full volume. A dispensing pressure for the fluid is achieved only in the delivery chamber 28, and does not affect the main reservoir 12. Therefore, the high pressure associated with dispensing cement is limited to a small area of the dispensing system 10, namely the dispensing chamber 28.

Figure 3:
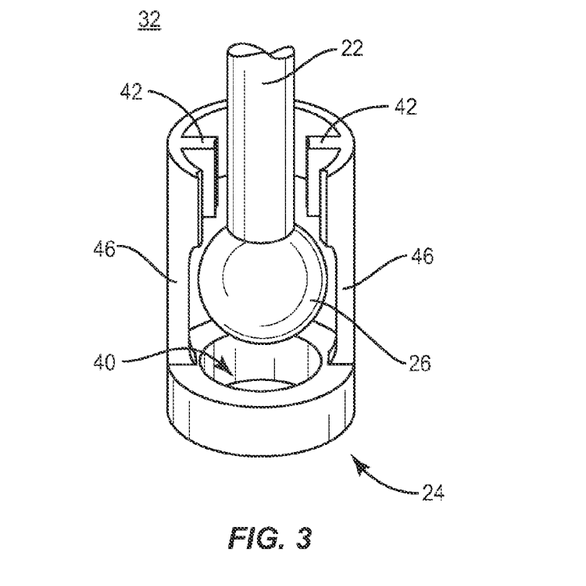
FIG. 3 is a perspective view of the end portion of the piston rod and the sleeve when the piston rod is retracted to enable a delivery chamber to be filled in accordance with the present principles.
Figure 4:
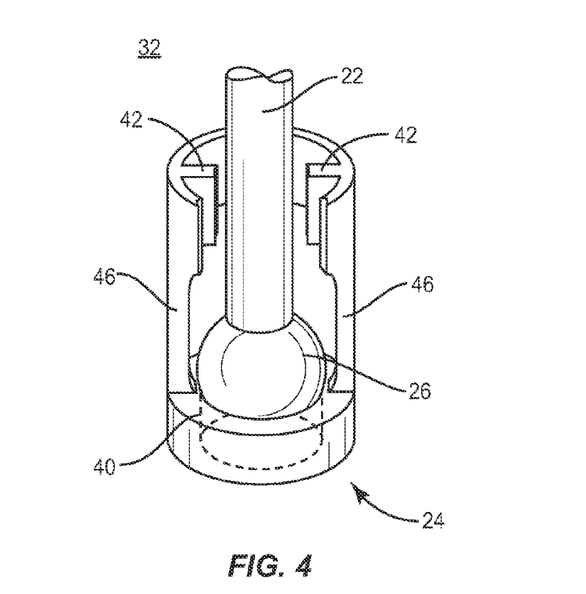
FIG. 4 is a perspective view of the end portion of the piston rod and the sleeve when the piston rod is advanced to seal off the delivery chamber and form a piston assembly for evacuating the delivery chamber in accordance with the present principles.

Referring to FIGS. 3 and 4, an illustrative piston assembly 32 is shown in its two modes of operation. FIG. 3 shows the piston rod 22 being retracted. The ball end 26 engages the sleeve 24 by contacting engagement portions 42. The ball end 26 includes a dimension larger than the piston rod 22. The portions 42 are supported by supports 46. Since the supports 46 and portions 42 do not completely occupy space around the ball end 26, when the ball end 26 is in the position shown in FIG. 3, cement can bypass the ball end 26 and enter the opening 40 into the delivery chamber (28) below. The engagement portions 42 occupy only a fraction of a surface area of the ball end 26 of the piston rod 22. This provides area for the flow of fluid (cement) passed the ball end 26 when the piston rod 22 is retracted.

FIG. 4 shows the piston rod 22 advanced so that the ball end 26 engages the opening 40 and forms a seal to prevent the passage of cement through the opening 40. Here, the sleeve and the ball end 26 form a piston to enable a volume of the delivery chamber (28) to be decreased with the advancing of the sleeve 24 and ball end 26.

While FIGS. 1-4 illustratively show a mechanism that provides for the formation of a valve and a piston in accordance with a direction that the mechanism is moved. It is contemplated that additional or other structures may be employed to provide the desired functionality in accordance with the present principles. It is envisioned that the ball end 26 and its corresponding mating surface on the opening 40 may have various configurations or shapes, such as, for example, oval, oblong, triangular, rectangular, square, polygonal, irregular, uniform, non-uniform, variable and/or tapered. The ball end 26 may include a hemisphere, a tear shape, a U-shape, etc.

It is further contemplated that the sleeve 24 may include other features instead of or in addition to the supports 46 and portions 42, such as for example, brackets, u-shaped frames, multiple column supports, structural pegs and the like. These features may have various dimensions, according to the requirements of a particular application.

In assembly, operation and use, delivery system 10, similar to the system described above, is employed with a surgical procedure, such as, for treatment or repair of bones. For example, as shown in FIGS. 1-4, delivery system 10, described herein, can be employed with a surgical treatment of an applicable condition or injury of an affected portion of a spinal column and adjacent areas within a body, such as, for example, vertebrae.

In use, to treat vertebrae, a medical practitioner obtains access to a surgical site including vertebrae in any appropriate manner, such as through incision and retraction of tissues. It is envisioned that delivery system 10 can be used in any existing surgical method or technique including open surgery, mini-open surgery, minimally invasive surgery and percutaneous surgical implantation, whereby vertebrae is accessed through a mini-incision, or sleeve that provides a protected passageway to the area. Once access to the surgical site is obtained, the particular surgical procedure can be performed for treating the disorder. An incision is made in the body of a patient and a cutting instrument (not shown) creates a surgical pathway for implantation of components of delivery system 10. A preparation instrument (not shown) can be employed to prepare tissue surfaces, as well as for aspiration and irrigation of a surgical region according to the requirements of a particular surgical application. Prosthetics and necessary hardware, screws, posts, pins, etc. may be installed.

The delivery system 10 accesses the surgical site along the surgical pathway(s). The delivery system 10 is employed to inject or deliver cement or other materials into or onto a bone or bones. In one embodiment, delivery system 10 provides an agent, which may be injected into the surgical site. The agent can be designed to leach out of the cement once it is cured either in a burst or over time so as to facilitate bone growth or treat the condition being addressed. For example, it is envisioned that the agent included in the cement may include bone growth promoting material. It is contemplated that the agent may include therapeutic polynucleotides or polypeptides. It is further contemplated that the agent may include biocompatible materials, such as, for example, biocompatible metals and/or rigid polymers, such as, titanium elements, metal powders of titanium or titanium compositions, sterile bone materials, such as allograft or xenograft materials, synthetic bone materials such as coral and calcium compositions, such as HA, calcium phosphate and calcium sulfite, biologically active agents, for example, gradual release compositions such as by blending in a bioresorbable polymer that releases the biologically active agent or agents in an appropriate time dependent fashion as the polymer degrades within the patient. Suitable biologically active agents include, for example, BMP, Growth and Differentiation Factors proteins (GDF) and cytokines. The components of delivery system 10 can be made of radiolucent materials such as polymers. Radiomarkers may be included for identification under x-ray, fluoroscopy, CT or other imaging techniques. It is envisioned that the agent may include one or a plurality of therapeutic agents and/or pharmacological agents for release, including sustained release, to treat, for example, pain, inflammation and degeneration.

It is envisioned that the use of microsurgical and image guided technologies may be employed to access, view and repair spinal deterioration or damage, view and repair fractures or damage to bones in the extremities of a patient, with the aid of delivery system 10. Upon completion of the procedure, the surgical instruments and assemblies are removed and the incision is closed.

It will be understood that various modifications may be made to the embodiments disclosed herein. Therefore, the above description should not be construed as limiting, but merely as exemplification of the various embodiments. Those skilled in the art will envision other modifications within the scope and spirit of the claims appended hereto.

What is claimed is:

1. A delivery system comprising:
a reservoir having a proximal end and a distal end, adapted for storing at least a first portion of a fluid, and configured for applying a distal force on the first portion of the fluid toward the distal end;
a piston rod shaft having a proximal end, a distal end, and a first dimension, and configured for reciprocally moving through the reservoir in a distal direction and a proximal direction;
an end portion connected to the distal end of the piston rod shaft, the end portion having a second dimension larger than the first dimension of the piston rod shaft;
a sleeve having an upper opening in communication with the distal end of the reservoir, the upper opening having a third dimension configured to permit passage therethrough of the piston rod shaft, and a lower opening, having the second dimension, configured to be closed by insertion therein of the end portion; and a delivery chamber in communication with the lower opening of the sleeve and configured for holding a second portion of the fluid;

wherein the sleeve, the piston rod shaft, and the end portion are configured to elect the second portion of the fluid from the delivery chamber when the piston rod shaft and the end portion are advanced in the distal direction; and wherein the sleeve, the piston rod shaft, and the end portion are configured to allow a portion of the first portion of the fluid in the reservoir, under the distal force applied to the first portion of the fluid in the distal direction by the configuration of the reservoir, to move in the distal direction into the delivery chamber, when the piston rod shaft and the end portion are retracted in the proximal direction.

2. The delivery system as recited in claim 1, wherein the end portion includes a ball shape configured to engage the lower opening in the sleeve to form a valve, the valve being opened when the piston rod shaft is retracted in the proximal direction, and the valve being closed when the piston rod shaft is advanced in the distal direction into contact with the lower opening in the sleeve.

3. The delivery system as recited in claim 1, further comprising a biased reservoir piston configured to pressurize the first portion of the fluid in the reservoir toward the distal end.

4. The delivery system as recited in claim 1, wherein the biased reservoir piston is biased by a spring disposed within a body, the body being in fluid communication with the reservoir.

5. The delivery system as recited in claim 1, wherein the lower opening is configured to correspond with a shape of the end portion such that a seal is formed when the lower opening and the end portion are forced together.

6. The delivery system as recited in claim 1, wherein the sleeve includes at least two opposing supports that are configured to engage the end portion.

7. The delivery system as recited in claim 6, wherein the supports each include an engagement portion that occupies a fraction of a surface area of the end portion.

8. The delivery system as recited in claim 1, wherein the delivery chamber forms an internal bore and the sleeve includes an outer portion that engages the bore.

9. The delivery system as recited in claim 1, wherein a piston formed by the sleeve, the piston rod shaft, and the end portion is configured to force the second portion of the fluid to be ejected from the delivery chamber.

10. The delivery system as recited in claim 1, wherein the delivery chamber is configured to fluidly communicate with a fitting to dispense the second portion of the fluid from the fitting.

11. The delivery system as recited in claim 10, wherein the fitting is configured to receive one of a syringe, needle or a nozzle for dispensing the second portion of the fluid.

12. The delivery system as recited in claim 1, wherein the end portion includes a rounded shape for engaging the lower opening in the sleeve.

13. The delivery system as recited in claim 1, wherein the fluid includes bone cement, the bone cement including poly (methyl methacrylate).

14. The delivery system as recited in claim 1, wherein when the piston rod shaft is advanced less than a full stroke, the delivery chamber is configured to receive the portion of the at least the first portion of the fluid, occupying less than a full volume of the delivery chamber.

15. The delivery system as recited in claim 1, wherein the piston rod shaft is configured to be activated remotely from outside an imaging area.

16. The delivery system as recited in claim 1, wherein a dispensing pressure for the fluid is achieved only in the delivery chamber.

17. The delivery system as recited in claim 1, wherein the piston rod shaft is configured to be reciprocated to alternately fill and dispense the respective portion of the fluid from the delivery chamber.

18. The delivery system as recited in claim 1, wherein the distal force applied to the first portion of the fluid in the reservoir is applied by a spring-loaded reservoir piston, the spring being adapted to bias the reservoir piston in the distal direction.

19. A delivery system comprising:

a reservoir having a proximal end and a distal end for storing a first portion of a fluid;

a biased reservoir piston configured to pressurize the first portion of the fluid in the reservoir toward the distal end, the reservoir piston being biased by a spring disposed within a body in fluid communication with the reservoir;

a piston rod reciprocally movable through the reservoir in a distal direction and a proximal direction, the piston rod having a piston rod shaft and a ball-shaped end portion at a distal end of the piston rod shaft, the ball-shaped end portion having a dimension larger than a dimension of the piston rod shaft; and a sleeve configured to engage the ball-shaped end portion of the piston rod, the sleeve including an outer portion that contacts an internal bore of a delivery chamber, the delivery chamber including a second portion of the fluid, at least two opposing supports that are configured to engage the ball-shaped end portion of the piston rod and an engagement portion on each support being configured to occupy a fraction of a surface area of the ball-shaped end portion of the piston rod;

wherein the piston rod shaft, the ball-shaped end portion, and the sleeve are configured to elect the second portion of the fluid from the delivery chamber when the piston rod is advanced in the distal direction; and wherein the piston rod shaft, the ball-shaped end portion, and the sleeve are configured to permit a portion of the first portion of the fluid in the reservoir, under pressure from the reservoir piston in the distal direction, to move past the piston rod shaft and the ball-shaped end portion, through an opening in the sleeve and into the delivery chamber when the piston rod shaft and the ball-shaped end portion are retracted in the proximal direction.

20. A method for delivering bone cement, the method comprising:

utilizing a delivery system including a reservoir having a proximal end and a distal end, configured to store a first portion of the bone cement, and a spring disposed in the reservoir applying pressure to the first portion of the bone cement toward the distal end; a piston rod passing through the reservoir and having an end portion with a dimension larger than a dimension of a shaft of the piton rod reciprocally movable through the reservoir in a distal direction and a proximal direction; a sleeve having an upper opening in communication with the reservoir configured to engage the shaft of the piston rod with a clearance fit, and a lower opening configured to engage the end portion of the piston rod with an interference fit; and a delivery chamber in communication with the sleeve via the lower opening and configured to store a second portion of the bone cement; wherein when the piston rod is advanced in the distal direction, the end portion seals the lower opening in the sleeve, and ejects the second portion of the bone cement from the delivery chamber; and wherein when the piston rod is retracted in the proximal direction, the sleeve and the piston rod are configured to permit a portion of the first portion of the bone cement in the reservoir under pressure from the spring in the distal direction to move in the distal direction, into the delivery chamber through the upper opening and the lower opening of the sleeve; and reciprocating the piston rod to alternately fill and dispense the respective portion of the bone cement from the delivery chamber.

21. The method as recited in claim 20, wherein reciprocating includes at least partially retracting the piston rod in the proximal direction and subsequently at least partially advancing the piston rod in the distal direction to deliver the portion of the first portion of the bone cement, having a volume occupying less than a full capacity of the delivery chamber.

* * * * *

UNITED STATES PATENT AND TRADEMARK OFFICE
CERTIFICATE OF CORRECTION

| | | |
|---|---|---|
| PATENT NO. | : 9,095,394 B2 | Page 1 of 1 |
| APPLICATION NO. | : 13/456597 | |
| DATED | : August 4, 2015 | |
| INVENTOR(S) | : Click et al. | |

It is certified that error appears in the above-identified patent and that said Letters Patent is hereby corrected as shown below:

In the claims

Column 9, Line 5, Claim 1, delete "elect" and insert -- eject --, therefor.

Column 9, Line 26, Claim 4, delete "claim 1," and insert -- claim 3, --, therefor.

Column 10, Line 36, Claim 19, delete "elect" and insert -- eject --, therefor.

Column 10, Lines 55-56, Claim 20, delete "piton rod" and insert -- piston rod, --, therefor.

Signed and Sealed this
Twenty-fourth Day of May, 2016

Michelle K. Lee
*Director of the United States Patent and Trademark Office*